United States Patent [19]

Lewis et al.

[11] 4,066,680

[45] Jan. 3, 1978

[54] PROCESS FOR MAKING ALPHA,OMEGA-SILOXANEDIOLS

[75] Inventors: Richard N. Lewis, Tecumseh; Eugene R. Martin, Onsted, both of Mich.

[73] Assignee: SWS Silicones Corporation, Adrian, Mich.

[21] Appl. No.: 733,564

[22] Filed: Oct. 18, 1976

[51] Int. Cl.$^2$ ............................................... C07F 7/08
[52] U.S. Cl. ............................................... 260/448.2 E
[58] Field of Search ................................. 260/448.2 E

[56] References Cited

PUBLICATIONS

Noll, "Chemistry and Technology of Silicones," Academic Press, N.Y. (1968), pp. 95 and 108.

*Primary Examiner*—Paul F. Shaver

[57] ABSTRACT

Alpha,omega-siloxanediols are prepared from siloxanes by a two-step process. In the first step, the siloxane is converted to a linear alpha,omega-diacyloxysiloxane by heating with an acid anhydride and a carboxylic acid in the presence of acid clay. The diacyloxysiloxane is hydrolyzed to the siloxanediol by heating with an aqueous solution of a weak base.

8 Claims, No Drawings

PROCESS FOR MAKING ALPHA,OMEGA-SILOXANEDIOLS

This invention relates to alpha,omega-siloxanediols and more particularily to a process for their preparation.

It is known that linear alpha,omega-siloxanediols, hereinafter called siloxanediols, may be prepared by the hydrolysis of dimethyldichlorosilane. Depending on temperature, amount of water, the nature of solvent, it any, and catalysts, siloxanediols of a wide range of chain length may be obtained. However, it is difficult to obtain siloxanediols of very short chain lengths by this process, because of their tendency to condense to longer chains under the influence of the by-product acid. Normally hydrolysis produces an average chain length of over 30 dimethylsiloxane units, corresponding to a hydroxyl content of 1.5 percent or less. The process also produces a large amount, up to 50 percent or more, of cyclic siloxanes.

A somewhat better process involves equilibration of linear or cyclic siloxanes with dimethyldichlorosilane and an acid catalyst, to produce an alpha,omega-dichlorosiloxane, followed by hydrolysis to give the siloxanediol. By this method the hydroxyl content may be increased to about 2.5 percent, corresponding to a chain of about 18 dimethylsiloxane units. If a solvent is used the hydroxyl content may be increased to about 3 percent (about 15 dimethylsiloxane units). The problem lies in the rapid condensation of the intermediate alpha-chloro-omega-siloxanol during the hydrolysis step; the shorter the chain, the more rapid the condensation.

Therefore it is an object of this invention to provide a process for the controlled preparation of siloxanediols of the formula $HO(R_2SiO)_nH$, in which at least 50 percent of the R groups are methyl, and up to 50 percent of the R groups are vinyl or phenyl, n is a number from 3 to 25, and the hydroxyl content is from about 1.8 to about 14 percent. It is another object of this invention to provide siloxanediols which are effective antistructure agents (softener fluids) for silicone rubber.

These objects, and others which will become apparent from the following description, are achieved, generally speaking, by heating cyclic and/or linear siloxanes with an acid anhydride and a carboxylic acid in the presence of an acid clay to produce an alpha,-omega-diacyloxysiloxane having the formula $R'COO(R_2SiO)_nOCR'$ where R, and n are the same as above and R' is a hydrocarbon radical of from 1 to 3 carbon atoms, removing the unreacted acid and acid clay, and heating the alpha,omega-diacyloxysiloxane with an aqueous solution of a weak base.

The cyclic siloxanes have the formula $(R_2SiO)_x$, in which x is a number of from 3 to 10, preferably from 3 to 6, and R is as defined above.

The linear siloxanes have the formula $$HO(R_2SiO)_yH \text{ or } R'COO(R_2SiO)_yOCR'$$

in which y has an average value of from 2 to 300 and preferably from 2 to 50.

The siloxanes may contain a minor amount of a silane of the formula $$R_2Si(OH)_2 \text{ or } R_2Si(OCOR')_2.$$

Examples of suitable cyclic siloxanes include cyclic dimethylsiloxanes of the formula $[(CH_3)_2SiO]_x$ where x is from 3 to 6; cyclic methyl vinyl siloxanes such as heptamethylvinylcyclotetrasiloxane and tetramethyltetravinylcyclotetrasiloxane; and cyclic methyl phenyl siloxanes.

Examples of suitable linear siloxanes include the hydrolysis products and cohydrolysis products of dimethyldichlorosilane, methylvinyldichlorosilane, methylphenyldichlorosilane, and diphenyldichlorosilane.

Examples of suitable silanes include dimethyldiacetoxysilane, methylvinyldiacetoxysilane, methylphenyldiacetoxysilane, diphenyldiacetoxysilane and diphenylsilanediol.

It will be understood that whenever a siloxane having a high vinyl or high phenyl content is used, another siloxane having a high methyl content is added so that the methyl groups will comprise at least 50 percent of the total R groups.

The carboxylic acids of this invention are preferably the water-soluble unsubstituted monobasic acids having from 2 to 4 carbon atoms. Likewise the acid anyhdrides are preferably those with from 4 to 8 carbon atoms. Examples of suitable acids and anhydrides include acetic, propionic, butyric, isobutyric, acrylic and crotonic.

When the siloxane is equilibrated with, for example, acetic anhydride the chain length of the resulting diacetoxysiloxane is determined mainly by the mole ratio of acetic anhydride to siloxane units, the reaction being essentially:

$$n(R_2SiO) + (CH_3CO)_2O \rightarrow CH_3COO(R_2SiO)_n COCH_3$$

where n is the same as above, and the mole ratio of $R_2SiO$ to acetic anhydride may be varied between 3:1 and 25:1.

The carboxylic acid acts as a solvent and cocatalyst, but has little effect on the equilibrium chain length. The amount used is not critical, but it should be between 2 and 20 percent of the total reaction mixture. In many cases one mole of acid per mole of anhydride is satisfactory.

The principal catalyst is an acid clay prepared by treating clay with sulfuric acid. Suitable grades include Filtrol 13 (fine) and Filtrol 24 (coarse) obtained from Filtrol Corporation. The amount required is not critical, but good results are obtained with from 0.5 to 2 percent of the total reaction mixture.

If the initial silane or siloxane has a high hydroxyl content some changes must be made in the ratio of reactants. Bearing in mind that two hydroxyl groups generate one molecule of water, which destroys one molecule of acid anhydride, the amount of the latter must be increased accordingly. In other words, for every mole of water formed by condensation, or which may be present as an impurity, one additional mole of acid anhydride must be employed. In some cases enough carboxylic acid is generated so that none need be added.

The equilibration times and temperatures are inversely related. Two to five hours at reflux temperature, approximately 140° C, is generally sufficient. When Filtrol 13 is used, about 10 hours is required at 130° C and 20 hours at 120° C. Slightly longer times are required with Filtrol 24. Shorter times are sufficient if the equilibration is carried out at temperatures up to 150° C under slight pressure, or if the amount of catalyst is increased. The reaction may be carried out at any temperature between 100° and 200° C, but the preferred range is from 120° to 150° C.

The equilibrated material is cooled to room temperature and the unreacted carboxylic acid is removed by washing several times with water. If desired, sodium chloride or other salt may be added to facilitate phase separation by increasing the density of the water layer. Normally the acid clay is wetted by the water and is removed with the water. Alternatively, it may be removed first by filtration.

The washed material still contains most of the acyloxy end groups, as well as some free carboxylic acid. At this stage, it is somewhat unstable, as any prematurely formed hydroxyl groups tend to condense with residual acyloxy groups, thus producing longer-chain siloxanes. The rate is somewhat variable, but in general there is only slight loss of end groups in one hour and very considerable loss in 24 hours. Thus the washing step should be completed with deliberate speed. In order to produce a stable product further hydrolysis is necessary. A siloxanediol of adequate stability is reached when the total of acyloxy groups and free carboxylic acid is reduced to less than 0.25 percent by weight of the siloxanediol.

Although hydrolysis of acyloxy groups is slow in neutral or acid solution it proceeds more rapidly as the pH is increased, especially if the temperature is also raised. Very rapid hydrolysis takes place in strongly alkaline solutions of pH 13 or more. Such a pH also causes condensation however, and severly reduces the final hydroxyl content. On the other hand, saturated sodium bicarbonate, which has a pH of 8.3, drops later to a pH of about 7.5 as the acid is neutralized, and gives incomplete neutralization even after 24 hours at room temperature. Somewhat better results are obtained with sodium carbonate and potassium carbonate solutions at room temperature, but even so, as the pH is raised beyond 10.5 some condensation occurs. In general the pH should be in the range of 8 to 11, and preferably in the range of 8.5 to 10.5.

Best results are obtained by heating with an aqueous solution of a weak base to a temperature between about 30 and about 105° C. Suitable weak bases include sodium bicarbonate, sodium carbonate, sodium sesquicarbonate, potassium bicarbonate, potassium carbonate and ammonium hydroxide.

The desired pH may be achieved with sodium bicarbonate by boiling the mixture. This causes evolution of carbon dioxide and the gradual conversion of bicarbonate to carbonate. Two hours of boiling with 20 percent sodium bicarbonate is sufficient to achieve substantially complete hydrolysis and neutralization with little condensation. There is one slight disadvantage to this process in that there is no control over the final pH. It tends to keep rising and eventually goes beyond 10.5, with resulting loss of hydroxyl groups.

Another way to achieve the desired pH is to heat with bicarbonate at a somewhat lower temperature, preferably 50° to 90° C, add a little carbonate to bring the pH to the desired level and heat a short time longer, e.g. for a half hour.

The process of this invention produces a homologous mixture of siloxanediols. If desired, the various siloxanediols, such as hexamethyltrisiloxanediol, octamethyltetrasiloxanediol and decamethylpentasiloxanediol can be separated from the mixture by fractional distillation.

The siloxanediols of this invention are particularly useful as antistructure agents in silicone rubber. They are useful as treating agents for inorganic surfaces to make them hydrophobic. They also are useful as chemical intermediates in the formation of other siloxanes.

In the following examples all parts are by weight unless otherwise specified.

EXAMPLE 1

The following materials were mixed together: 740 parts of octamethylcyclotetrasiloxane ($D_4$), 204 parts of acetic anhydride, 120 parts of acetic acid, and 40 parts of acid clay (Filtrol 13). The mixture was heated to reflux temperature and kept under reflux at 137.5°–139° C for 4 hours. It was then cooled, filtered, and analyzed by gel permeation chromatography, which showed that about 80 percent of the $D_4$ had been converted to a mixture of short, linear siloxanes averaging 6 to 7 siloxane units. Similar results were obtained from a sample taken after 2.5 hours. This material was washed with 1000 parts of 10 percent aqueous sodium chloride, then with a slurry of 900 parts of water and 100 parts of sodium bicarbonate, and finally with 1000 parts of aqueous sodium bicarbonate, at which point a strong odor of acetic acid was still present.

Seven portions of 100 parts each were hydrolyzed in 336 parts of water with added sodium carbonate or sodium bicarbonate. The conditions and results are summarized in the following table:

| Example | $Na_2CO_3$, parts | Temp., °C | Time, Hours | Final pH | OH, % | OAc, % |
|---|---|---|---|---|---|---|
| 1A | 26 | 30 | 6 | 9.7 | 5.55 | 4.70 |
| 1B | 39 | 30 | 6 | 9.9 | 6.83 | 2.60 |
| 1C | 52 | 30 | 6 | 10.2 | 6.52 | 2.07 |
| 1D | 36 | 60 | 4 | 9.87 | 6.24 | 0.09 |
| 1E | 31 | 60 | 4 | 9.75 | 6.20 | 0.13 |
| 1F | 26 | 70 | 5 | 9.56 | 6.34 | 0.04 |
| 1G | 22* | 70 | 5 | 8.66 | 6.70 | 0.21 |

*$NaHCO_3$ used.

It can be seen that hydrolysis was incomplete at 30° C, even when a large excess of sodium carbonate was used and the final pH of the water solution was above 10 (Example 1C). The high acetoxy (OAc) level results in a somewhat unstable material. Hydrolysis carried out at 60° C and 70° C was much more nearly complete and gave completely satisfactory products, even when the final pH was as low as 8.66 (Example 1G).

EXAMPLE 2

In similar fashion 444 parts of $D_4$, 56 parts of acetic anhydride, 30 parts of acetic acid, and 10 parts of Filtrol 13 were heated at reflux, 144° C, for 1 hour. A sample analyzed by gas chromatography showed the following (Ac=$CH_3CO$; D=$(CH_3)_2SiO$):

| | |
|---|---|
| AcOH | 19.04% |
| $D_3$ | 1.26% |
| $D_4$ | 14.20% |
| $AcOD_3Ac$ | 0.08% |
| $D_5$ | 8.44% |
| $AcOD_4Ac$ | 1.87% |
| $D_6$ | 2.84% |
| $AcOD_5Ac$ | 2.69% |
| $D_7$ | 0.67% |
| $AcOD_6Ac$ | 3.25% |
| $D_8$ | 0.44% |
| $AcOD_7Ac$ | 3.77% |
| $D_9$ | 0.44% |
| $AcOD_8Ac$ | 3.84% |
| $D_{10}$ | 0.16% |
| $AcOD_9Ac$ | 3.96% |

| -continued | |
|---|---|
| $D_{11}$ | 0.09% |
| $AcOD_{10}Ac$ | 4.11% |

Other linear diacetoxysiloxanes were observed in the range of 1 to 4 percent up to $AcOD_{19}Ac$. Similar results were obtained on a sample taken after 2 hours. In this case equilibration was essentially complete in 1 hour.

EXAMPLE 3

A mixture of 250 parts of $D_4$, 17 parts of a methylvinyl siloxane $(MeViSiO)_x$, consisting of linear and cyclic siloxanes in a ratio of about 6:4, and having a viscosity of 100 cP; 50 parts of acetic anhydride; 23 parts of glacial acetic acid; and 5 parts of Filtrol 13 LM (low-moisture grade) was heated to 145° C in a closed vessel for 5 hours with continuous agitation. The mixture was then cooled and washed three times with aqueous sodium bicarbonate at about 40° C, whereupon most of the acid clay was found to have been removed with the water. The washed fluid was then heated to 80° C with a slurry of 100 parts of sodium bicarbonate in 460 parts of water. After 3 hours 10 parts of sodium carbonate was added and heating was continued for another 2 hours. The aqueous phase was drawn off while still hot, and found to have a pH of 9.8. The final siloxanediol was analyzed, with the following results:

| Hydroxyl content | 4.51 percent |
|---|---|
| Vinyl content | 2.14 percent |
| pH | 7.87 |
| Acetoxy (calculated as acetic acid) | 122 ppm |
| Viscosity | 32.6 cSt |
| Specific gravity | 0.979 |

This siloxanediol was tested in a silica-filled silicone rubber and found to be an effective antistructure agent. On a weight basis it is much more effective than other siloxanediols having a hydroxyl content in the rang of 2-3 percent.

What we claim is:

1. A process of making alpha,omega-siloxanediols of the formula $HO(R_2SiO)_nH$, in which at least 50 percent of the R groups are methyl and the remaining R groups are selected from the class consisting of vinyl and phenyl and n is a number of from 3 to 25, which comprises heating an alpha,omega-diacyloxysiloxane with an aqueous solution having a pH of from 8 to 11 to a temperature of at least 50° C.

2. The process of claim 1 in which the alpha,omega-diacyloxysiloxane is prepared by the equilibration of siloxanes with an acid anhydride having from 4 to 8 carbon atoms in the presence of a carboxylic acid having from 2 to 4 carbon atoms and acid clay.

3. The process of claim 1 wherein the alpha,omega-diacyloxysiloxane has the formula $R'COO(R_2SiO)_nOCR'$ in which at least 50 percent of the R groups are methyl and the remaining R groups are selected from the class consisting of vinyl and phenyl groups, R' is a hydrocarbon radical having from 1 to 3 carbon atoms and n has an average value of from 3 to 25.

4. The process of claim 1 in which the diacyloxysiloxane is heated with aqueous sodium bicarbonate for at least two hours at a temperature of at least 50° C.

5. The process of claim 4 in which the diacyloxysiloxane is heated with boiling aqueous sodium bicarbonate until the pH is approximately 10.

6. The process of claim 4 in which the diacyloxysiloxane is heated with aqueous sodium bicarbonate for at least two hours at a temperature of from 50° C to 90° C and then further heated with sufficient sodium carbonate to bring the pH to about 10 until the sum of the acyloxy groups and the free carboxylic acid is less than 0.25 percent.

7. A process for making alpha,omega-diacyloxysiloxanes which comprises heating a siloxane with an acid anhydride having from 4 to 8 carbon atoms in the presence of a carboxylic acid having from 2 to 4 carbon atoms and acid clay for at least 1 hour at a temperature of from 120° C to 150° C.

8. The process of claim 3 wherein the alpha,omega-diacyloxysiloxane is alpha,omega-diacetoxysiloxane.

* * * * *